Figure 1:
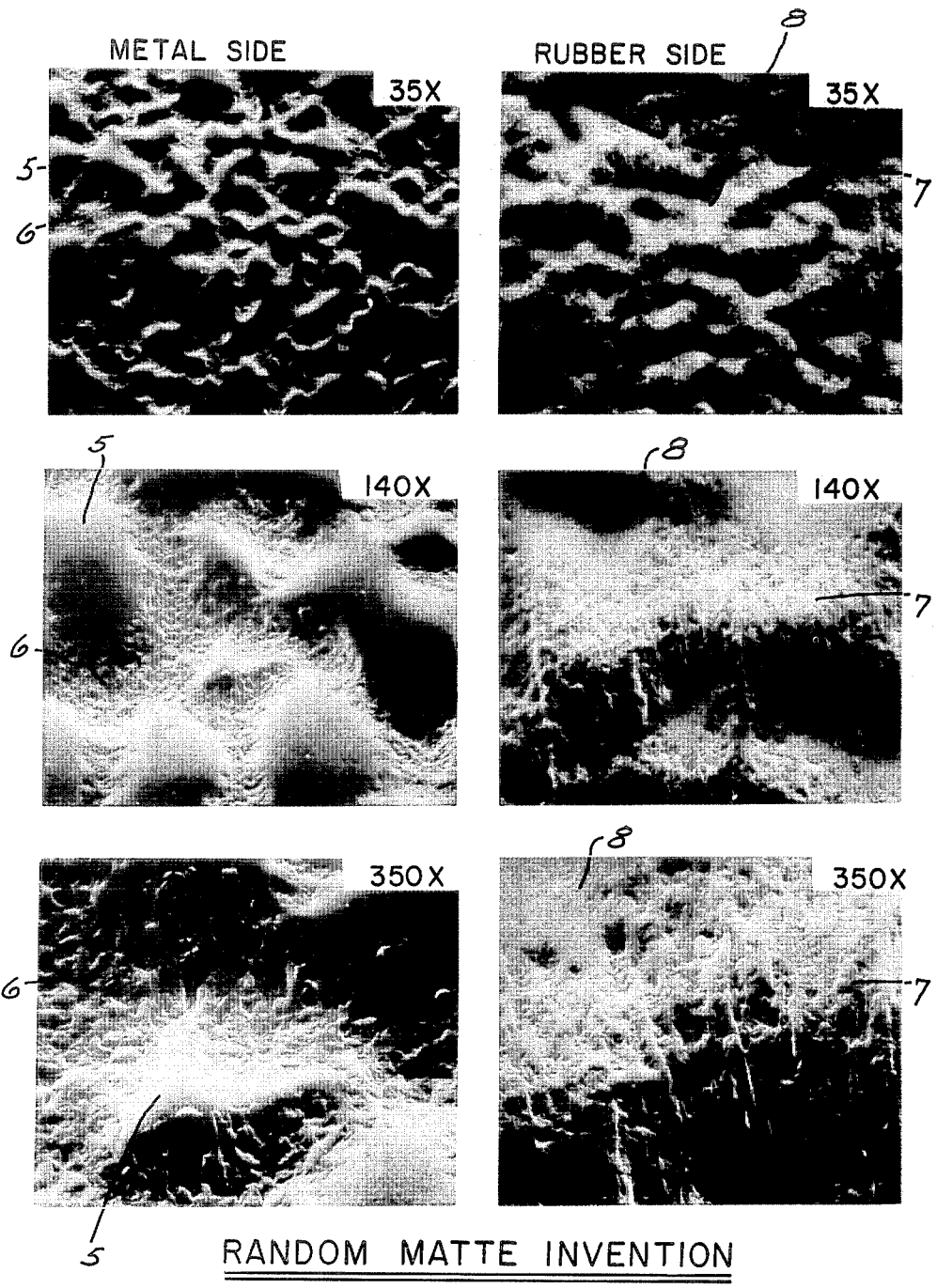

United States Patent [19]

Cancio et al.

[11] Patent Number: 4,546,029

[45] Date of Patent: Oct. 8, 1985

[54] RANDOM EMBOSSED MATTE PLASTIC FILM

[75] Inventors: Leopoldo V. Cancio; Pai-Chuan Wu, both of Cincinnati, Ohio

[73] Assignee: Clopay Corporation, Cincinnati, Ohio

[21] Appl. No.: 621,558

[22] Filed: Jun. 18, 1984

[51] Int. Cl.$^4$ ............................ B32B 1/00; B32B 3/30
[52] U.S. Cl. .................................. 428/141; 428/156; 428/179; 428/220
[58] Field of Search ............... 428/141, 156, 179, 220; 264/284, 293

[56] References Cited

U.S. PATENT DOCUMENTS

| | | | |
|---|---|---|---|
| 3,484,835 | 12/1969 | Trounstine et al. | 428/179 |
| 3,911,187 | 10/1975 | Raley | 428/156 |
| 3,950,480 | 4/1976 | Adams et al. | 264/284 |
| 4,376,147 | 3/1983 | Byrne et al. | 428/156 |
| 4,436,520 | 3/1984 | Lipko | 428/156 |

*Primary Examiner*—Paul J. Thibodeau
*Attorney, Agent, or Firm*—Wood, Herron & Evans

[57] ABSTRACT

A plastic film having a random embossed matte finish is provided. The random embossed matte film may be wound very easily into rolls and the roll contour achieved has superior uniformity. In addition, the film provides relatively equal tape adhesion and gloss properties on both sides which make it especially suitable for use in articles such as disposable diapers or underpads. Another advantageous property which renders it especially suitable for diaper conversion operations is its very low degree of edge curl. The thin film provides a totally different appearance as compared to conventional diaper films in that the overall appearance is a dull matte finish, but nonetheless having slight sparkles of brilliance throughout the surface, and it further provides a softer feel.

7 Claims, 3 Drawing Figures

METAL SIDE    RUBBER SIDE

U.S. PAT. NO. 4,376,147 MATTE

CONVENTIONAL MATTE

RANDOM EMBOSSED MATTE PLASTIC FILM

BACKGROUND OF THE INVENTION

Beginning several decades ago, plastic film began to achieve wide spread use in the fabrication of many useful articles, quite often as a replacement for woven fabrics. Early in the development of plastic film as a substitute for woven fabrics, patterns were created by imposing the image of a woven fabric into a film during the process of making the film. Wire screens, along with other mechanical implements, were later employed to create plastic films having various designs. As technology developed, metal rolls having engraved patterns were employed in the production of embossed plastic films which would simulate various designs. During this period of time, the person of ordinary skill in the art who made useful articles from plastic film, typically disposable diapers, covers, water repellent clothing, and the like, worked with the film on machinery and observed or studied its characteristics. Refinements or adjustments in the machinery as well as the material took place in order to produce useful articles from such embossed plastic films on high speed production machinery.

U.S. Pat. No. 3,484,835 which issued in 1969 is directed to a plastic film embossed with a pattern simulating a woven taffeta design and the film had a specially desirable characteristics of edge curl resistance during machine processing into useful articles. Embossed plastic film disclosed in this patent offered significant improvement over the earlier taffeta design which existed in the prior art. The embossed plastic film having edge curl resistance was characterized by a series of bosses and channel-like areas, spaced apart by about 10 mils with bosses protruding to a height within the range of about 3 to 4 mils and, on the opposite side, a series of depressed areas and ridges were created.

The simulated taffeta design disclosed in the above mentioned patent is only an example of many different designs created and employed by film fabricators in their effort to simulate woven fabrics or achieve other various visual appearances and physical properties which were advantageous from a manufacturing or consumer standpoint. Another one of such many designs is referred to in the art as a matte finish. A matte finish have heretofore been characterisized by a rather dull finish on a plastic film with no visually perceptible pattern. Matte finishes have been produced in films by the employment of sand-blasted embossing rollers. With the advancement of technology including new formulations in polymer compositions of the polyolefin type, particularly polyethylene, polypropylene and polybutadiene, the problem of handling various films has become complex. While there is a considerable amount of knowledge available to a person of skill in this art, behaviors of polymers, or their properties under various physical conditions, such as machine stress and other conditions, are not readily understood. One might say the plastic film technology is, indeed, more of an art than a science and experience has proven that problems in this area of the art are not as easily understood or solved owing to the unknown factors in handling such polymeric compositions under machine stress either in the manufacture or fabrication of such polymers into useful articles.

In connection with matte films, a number of problems have existed, particularly the difficulty in achieving gloss control and satisfactory winding characteristics as the matte film is being handled and wound at high speeds on machinery. These problems are further complicated by the desirability to obtain other balanced characteristics in matte film such as good tape adhesion values, soft or cloth-like hand, low coefficient of friction properties, among other advantages. U.S. Pat. No. 4,376,147 which issued in 1983 is directed to an embossed thermoplastic polyolefin film simulating a matte finish having excellent winding characteristics without edge curl, extremely low gloss even on both sides and good tape adhesion values, among other advantages, theretofore unachieved in prior matte films. In contradistinction to the prior art sand-blasted matte films, the film of the U.S. Pat. No. 4,376,147 has an embossed pattern comprising embossed lines or channel-like areas which are parallel to the free lengthwise edges of the film. The embossed lines provide a generally rectangular pattern with parallel and transverse lines numbering within the range of 150 to about 300 lines per inch. Employing such an embossed pattern, the surface of the film appears to the unaided eye as a very dull surface. Up to that point in the state of the art the matte film of the mentioned patent achieved a balance of physical surface characteristics theretofore unachieved in known matte films. As in any developing art, especially the production of plastic film, there is a constant need for further improvements to provide economies and advantageous properties in the resultant films. Accordingly, further improvements are desired.

SUMMARY OF THE INVENTION

This invention is directed to a random embossed thermoplastic polyolefin film simulating a matte or dull finish having excellent roll or winding characteristics and processability without edge curl. Moreover, among its other important attributes, heretofore unachieved in prior art diaper matte films is relatively equal tape adhesion on both sides of the random embossed film. This is an important new feature in diaper films which enables diapers to be used more effectively and conveniently without tearing the film. The thermoplastic matte films of this invention are relatively thin, particularly on the order of about 0.5 to about 1.5 mils. The film, that has been found to provide the desired dull surface or matte finish, has an embossed depth on the order of about 0.4 to about 2 mils depending upon film thickness. The random pattern comprises an asymmetric arrangement of asymmetrically raised bosses and depressed areas on one side of the film, and correspondingly, underlying asymmetrically depressed areas and raised bosses on the opposite side of the film. The asymmetric bosses and depressions are of such height and area on the surfaces of both sides of the film such that the unaided eye of an observer does not detect any pattern in the film, even though it is an embossed random pattern. In other words, the embossed pattern appears as an identically dull surface on both sides of the film. Still there is a very slight sparkle in the film surface. These properties are critically achieved in the obtainment of the advantages of this invention by randomly embossing a plastic film of about 0.5 to about 1.5 mils in thickness to an embossed depth of about 0.4 to about 2 mils. In the presently preferred form, the asymmetric bases and depressions about equally cover the surface area and range from a minimal average dimension in width or length of several mils to perhaps about 20 mils. On the average, 10-15 mil boss or depression areas are obtained, but it is to be understood that such are very random and these areas interconnect with one another. Such a combination of design and embossed depth has been unachieved in plastic films and, quite surprisingly, a unique balance of physical properties has been obtained.

In addition to the mentioned advantages, other unique features of the random embossed matte film of this invention include a totally different visual appearance as compared to conventional diaper films. While the film appears to the unaided eye as a rather dull surface with no visually perceptible embossed pattern, as mentioned, it tends to have a slight sparkling and pleasing appearance. Furthermore, the film provides a softer feel or cloth-like hand. Among its other properties, significant differences in the coefficient of friction on one side as compared to the other are achieved. Such differences permit processing advantages and different handling of the film if desired.

The matte film is made from suitable plastic materials, preferably of the thermoplastic type and particularly polyethylene, polypropylene, polybutadiene, polystyrene, polyester, copolymers of such polyolefins such as ethylene vinyl acetate copolymers, or modified polyolefin polymers such as polyethylene or polypropylene modified with conventional fillers, stabilizers, additive and the like. As mentioned above, the thickness of the films are on the order of about 0.5 to about 1.5 mils. It is critically important, however, that an embossing depth on the order of about 0.4 to about 2 mils is achieved in the film, depending on film thickness, to obtain the balanced properties heretofore unachieved in prior art films. A preferred polyolefin film is a low-to-medium density polyethylene. These plastic films can be embossed with the design of this invention according to any one of a number of well known techniques. A preferred method involves the introduction of thermoplastic material in a plastic state between usually a steel embossing roll and a smooth resilient roll or rubber roll which form a nip for embossing film. These techniques are considered conventional and are embodied herein by reference.

The invention will be further understood with reference to the drawings in which:

FIG. 1 is a series of magnified photographic views of the random embossed matte film of this invention from a top (metal embossing roll side) and the underside (rubber roll side) of the film.

Figure 2:
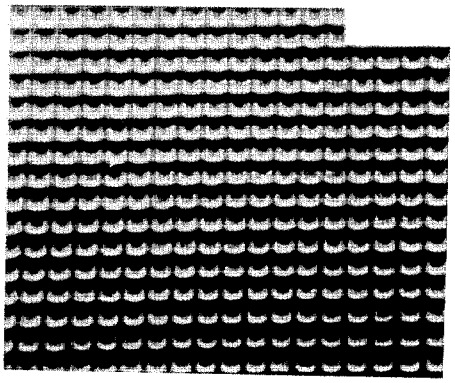
Figure 2:
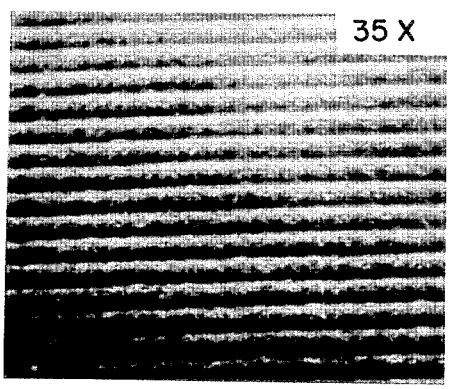
Figure 2:
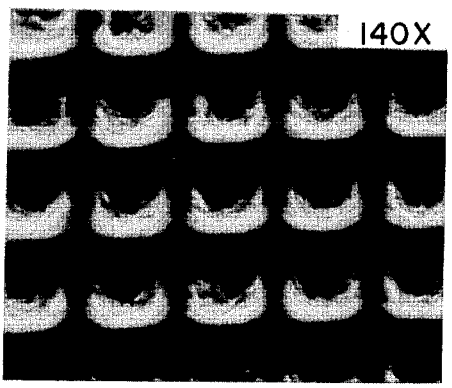
Figure 2:
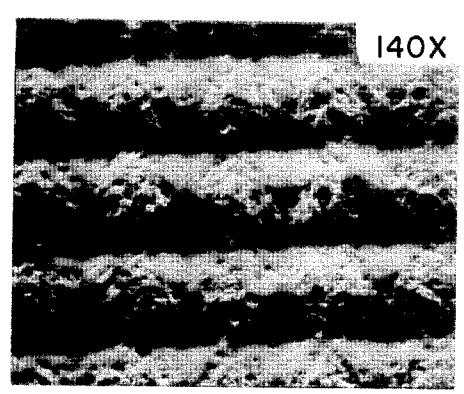
Figure 2:
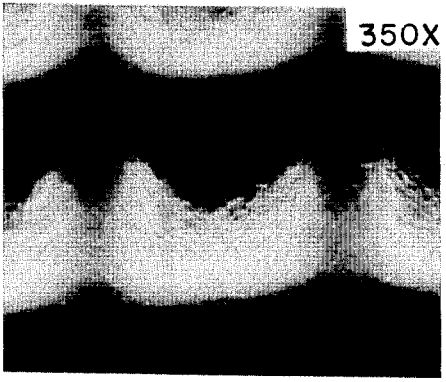
Figure 2:
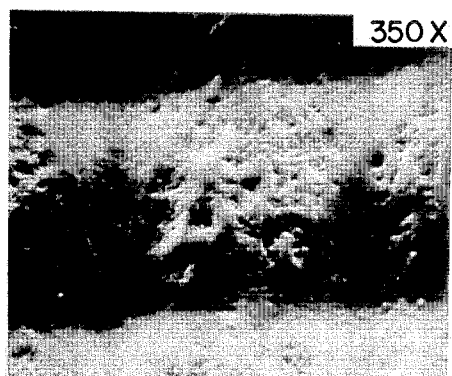

FIG. 2 is a series of magnified photographic views of the symmetrical embossed matte film of U.S. Pat. No. 4,376,157.

Figure 3:
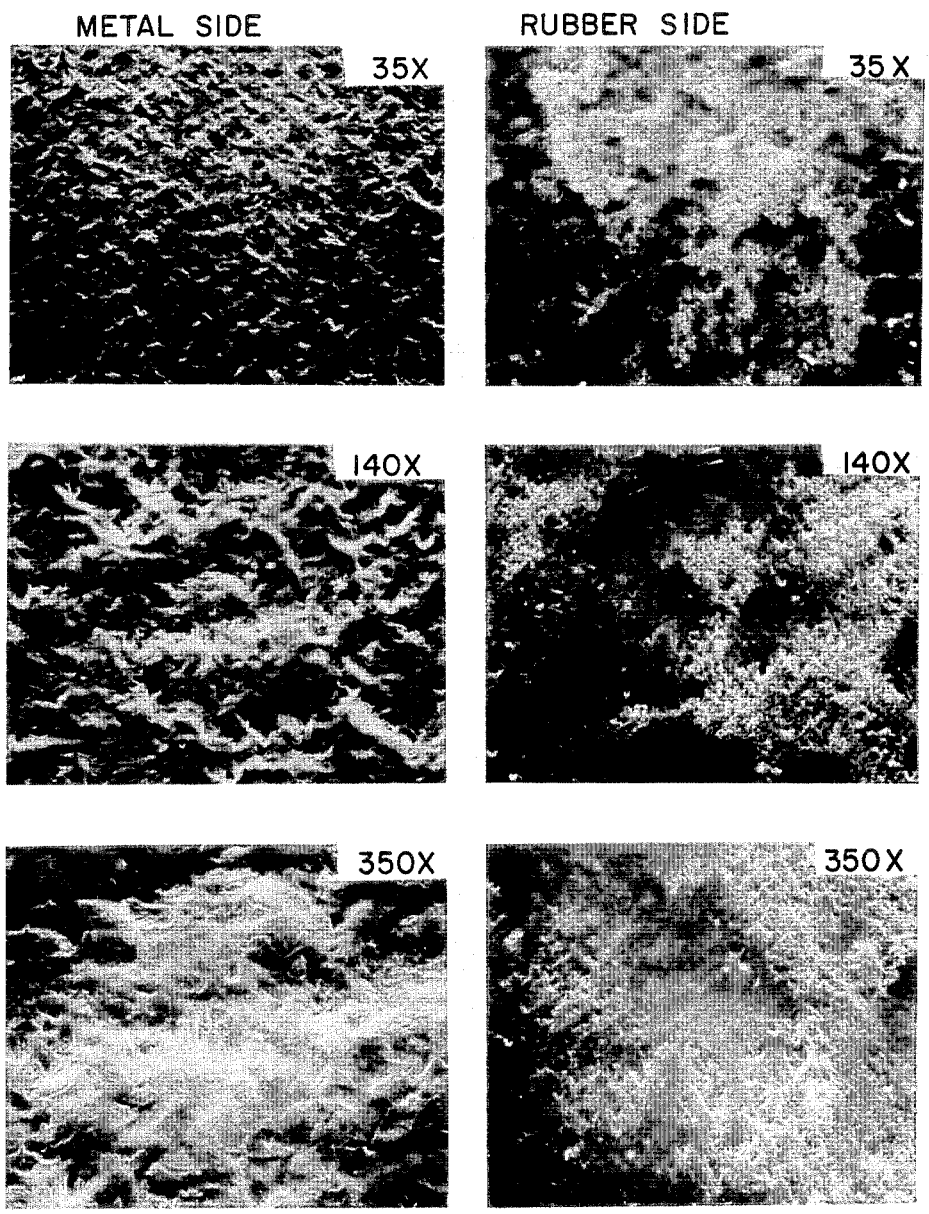

FIG. 3 is a series of magnified photographic views of a conventional matte film employing a sand-blasted embossing roller.

With reference to the photographs of FIG. 1, a polyethylene film is shown in top view on the metal roll side of the film as exhibited by the series of photographs on the left hand side of FIG. 1 in increasing magnification from about 35X, 140X or 350X magnification. On the right hand side of FIG. 1, the underside or rubber roll side of the film is exhibited in the series of photographs with increasing magnification over the same order of magnitude as its corresponding metal roll side. With reference to the top view of the plastic film, asymmetric bumps or bosses 5 which are shown separated by asymmetric depressed areas 6. This random embossed pattern provides the visual appearance of a dull surface even though the pattern is an embossed pattern under magnification having depressions between the bosses. On the underside or rubber roll side of the plastic film as shown by the series of photographic magnifications on the right side of FIG. 1, the bosses and depressed areas on the top side of the film overlie a series of depressions 7 and bosses 8 on the opposite side of the thinly embossed film. The photographic representations of the underside or rubber roll side of the film are not intended to correspond exactly with the photographed top or metal roll side of FIG. 1. Nevertheless, it is to be understood that the top side random pattern of asymmetric bosses and depressions has corresponding depressions and bosses on the underside of the film. The random pattern is actually formed by an engraving roll having an irregular distribution of depressions and raised areas. The embossing roll is actually formed with an engraving tool which is the reverse image of the embossing roll. The engraver's tool is made by employing a pointed punch and hammer. The pointed punch is used to individually form the depressions on the surface of the engraver's tool by hand punching such depressions in irregular distribution over the surface of the tool. Then, by the process of engraving, the master tool enables the embossing roll to be made and such details are not pertinent to this invention. Rather, with reference to the drawing, one may observe that the metal roll side of the embossing roll is mirrored in the plastic film. The hand punch holes in the roll provide the irregular depressions which are mirrored in the metal roll side of the plastic film. The irregular sizes of the bosses 5 and the depressed areas 6 are shown. This random embossed matte pattern may thus be produced by providing what is known to an engraver as an engraving roll which has been made with a matting tool by hand punching and engraving. Such details of manufacturing the engraving roll with a matting tool are well known. However, the asymmetrical patterns of bosses 5, 7 and depressed areas 6, 8 which provide the dull surfaces have a critically important depth of about 0.4 to about 2 mils in a thin film (about 0.5 to 1.5 mils thick) in order to achieve the advantages of the invention. For instance, a random embossed film of this invention preferrably has an embossed depth of about 1 mil in a 1 mil thick film. The engraving roll must be engraved to a depth of about 1.5 to 2.5 mils to achieve the embossed film. The asymmetrical bosses and depressions in the film of FIG. 1 have an average size ranging from about 3 to about 20 mils in width or length. Normally the embossed depth is slightly less than the engraved depth of the metal engraved roll.

The "embossed depth" is determined by (a) measuring the average overall cross-sectional thickness of film from the top side of the bosses to the opposite undermost ridges (or bosses) on the underside, (b) measuring or determining the average film thickness and subtracting (a) from (b). This measurement may be made in a number of manners. For instance, a standard 1 inch micrometer may be used in a manner known to those of ordinary skill in the art, to measure the embossed depth by measuring (a) and (b). For purposes of this invention the film thickness may be calculated, based on the film density. The embossed depth is the difference between the film embossed gauge as measured by a micrometer and the film thickness calculated on the basis of film density. The film embossed gauge was measured by a TMI Model 549M low load micrometer with a 2 inch diameter anvil.

The random embossed pattern as photographically depicted on a magnified basis in FIG. 1 has a number of advantages as indicated above. The pattern enables the obtainment of excellent roll contouring and it allows the film to be wound more easily. A very low degree of edge curl is achieved with the random bossed film which is very advantageous in diaper conversion operations. Furthermore, and quite unexpectedly, there are balanced tape adhesion values on both sides of the film. Among its other unique features, the film has a very good and low gloss on both sides which is a very good advantage from the practical standpoint because either side can be used in converting operations. Furthermore, the relatively equal tape adhesion values on both sides enable the film to be converted on either side into diapers. In comparison to other films, the film feels softer. At the same time, the film has significant differences in coefficient of friction on one side of the film versus the other, which can facilitate processing in special situations.

The random embossed matte pattern is formed, for example, by embossing a plastic film with a system of embossing rollers. One of the rolls is a steel roll whose surface is engraved with a pattern of protrusions which is commonly referred to as a male embossing roll. On the other hand, a female pattern may be engraved into the rolls by a series of depressions. A female pattern is created, for instance, by engraving the depressions or "pins down" into the steel roll to a depth of approximately 0.001 to 0.003 inch, depending on the thickness of the film which is embossed. As developed above, the steel tool engraved pattern will substantially correspond to the metal side of the embossed film, being appreciated that exact conformance will usually not be achieved. With reference to the photographs of FIG. 1, it will be appreciated by one of ordinary skill in this art that the bosses and channel-like areas are formed in the film surfaces such that there are smooth transitions between the asymmetrical bosses 5 and depressions 6 on the top side of the film. The same is true for the underside depressions 7 and bosses 8. In order to achieve the matte finish and physical properties of this invention, the boss depth indicated above must critically be between about 0.4 to about 2 mils with a film thickness on the order of about 0.5 to about 1.5 mils. The embossing depth is achieved by an embossing system of a rubber roll into which the steel roll pattern is impressed during the formation of the film by the usual technique of slot-die extrusion. The speed of the rubber and steel rolls is maintained to permit continuous embossing of the film for subsequent take-up on a wind-up roller.

In preferred form of the invention, low to medium density polyethylene, for instance, is formed into a matte film by a slot-die extrusion means. For example, the low to medium density polyethylene material is heated to a temperature of about 300° to 500° F. and then introduced in a web form through a slot into the nip of the steel and rubber roll system referred to above. The plastic material, upon being introduced between the nip of the rolls, is film-formed and at the same time textured with the random embossed pattern of the steel embossing roll. Under suitable embossing pressure of for instance of about 75 to 120 pounds per linear inch, a thin film having the embossed design may be produced. In achieving the preferred film thickness of between about 0.5 to about 1.5 mils, along with the necessary embossed depth of about 0.4 to about 2 mils, conditions are controlled in a manner well within the skill of those knowledgeable in the art of producing embossed films with an understanding of the disclosure of this invention. The factors which are considered may be varied depending upon the plastic material used and the characteristics to be obtained in the resultant film. Thus, process conditions which are obviously controlled to produce embossed film include temperature, pressure exerted between the nip of the embossing roller system, the depth of the engraved design on the steel roll and the hardness of the rubber roll.

For comparison with the random embossed pattern of this invention, FIGS. 2 and 3 have been provided show the conventional sand-blasted matte film (FIG. 3) and the symmetrically patterned matte film of the U.S. Pat. No. 4,376,147 (FIG. 2). By comparison with the embossed symmetrical pattern of the U.S. Pat. No. 4,376,147 which produces a matte finish, the pattern of this invention is random and asymmetrical. By further comparison with the film produced by sand-blasted roller according to the prior techniques, the random embossed film of this invention has a much greater embossed depth of about 0.4 to about 2 mils. Such embossed depths were incapable of being achieved in films produced by sand-blasted rollers. At most perhaps depths up to about 0.2 mils have been achieved by sand-blasted rolls. Thus, even though a random pattern has been produced by a sand-blasted roller, no random embossed film has been achieved especially with the depth of the inventive film. Furthermore, it has been found that even with the matte pattern having a random design similar to this invention, but engraved to a depth of about 0.6 mil in a 1 mil film, the advantages of this invention are not achieved. A critical relationship of embossed depth and film thickness must exist to achieve the winding characteristics, roll contour, gloss and tape adhesion values, among other advantages of this invention. A comparison of the random embossed matte film of this invention, the prior patent film mentioned above and the conventional film produced by the sand-blasted roller is made with reference to the following TABLE.

In connection with each of the film samples, the values for tape adhesion (TAV), coefficient of friction (COF) and gloss according to the following techniques were determined.

Tape Adhesion Value (TAV)—The TAV was a measure of the force required to peel a 1 inch wide standard fastening tape from the sample of each of the three mentioned films of FIGS. 1–3 as measured by hanging a static weight from the standard fastening tape which in turn is secured to the diaper film sample of the test. The weight was increased in regular increments until the tape peeled off the film sample. The TAV expressed in grams was calculated from a recorded time and weight and appears in the TABLE.

Coefficient of friction (COF)—The COF was the measure of the force required to move a small 2½ inch square sled weighing 200 grams as it traveled over a plane surface. The sled and the plane surface were covered with the test material of each of the films under examination so that the force measured was actually the frictional force between two layers of the film under examination according to the formula COF = Weight (200 grams)/Frictional Force and values obtained for each of the diaper films are recorded in the TABLE.

Gloss—The gloss values for each of the films are recorded in the TABLE as a measure of the shiny appearance of the film surface as obtained by stacking layers of each of the film samples and placement of the stack under an incandescent light source furnishing an incident beam. The axis of the incident beam was 45° from the perpendicular to the film surface and the gloss values for each of the diaper films were obtained by reading a glossy meter.

TABLE

DIAPER FILMS EXTRUDED BY USING INVENTION RANDOM EMBOSSED (FIG. 1) VS. U.S. PAT. NO. 4,376,147 FILM (FIG. 2) VS. CONVENTIONAL MATTE (FIG. 3)

| | | FIG. 1 | FIG. 2 | FIG. 3 |
|---|---|---|---|---|
| RUBBER ROLL SIDE | TAV (GRAMS) | 360 | 330 | 530 |
| | COF | 0.6-0.8 | 0.6 | 0.7 |
| | GLOSS (45°) | 7 | 5-6 | 14-22 |
| METAL ROLL SIDE | TAV (GRAMS) | 250 | 100 | 365 |
| | COF | 1.5-2 | 1.0 | 1.2 |
| | GLOSS (45°) | 7 | 5-6 | 8-10 |

With reference to the TABLE, the advantageous properties of the random emboss film of this invention will be appreciated. The properties of the film are set forth as they relate to the application for diaper back sheets, for instance. As a general conclusion, it may be stated that the random emboss film (FIG. 1) of this invention is the only film providing a matte or dull surface with relatively equal properties of acceptable tape adhesion and gloss on both sides of the film for diaper back sheet applications. More particularly, in comparison to the embossed film of the U.S. Pat. No. 4,376,147 (FIG. 2), from a standpoint of a tape adhesion value, one will observe that only the rubber roll side of the film having a TAV of 330 is acceptable whereas the 100 TAV value on the metal roll side of the film is unacceptable. In contrast, the random emboss film of this invention has a TAV on the rubber roll side of 360 and a TAV of 250 on the metal roll side and, for practical applications, these are substantially equal and acceptable tape adhesion values for both sides of the film. In comparison to the conventional matte film (FIG. 3) produced by the sand-blasted roller, the same conclusion on tape adhesion value may be reached, namely, that the conventional matte film has an unacceptably high TAV on the rubber roll side of 530 even though the TAV of 365 on the metal roll side is acceptable. For practical applications, the significance of the tape adhesion value is understood with reference to its relationship to practicality. For instance, TAV is a measure of the diaper back sheet's ability to be tape-secured to itself, and the diaper to be secured to the infant by the mother. A TAV value of 530 is too high because if one tries to remove the film due to misplacement or a misfit of the diaper to the infant, the mother cannot achieve this without tearing the film and ruining the diaper. On the other hand, for a tape adhesion value of around 300, namely about 250-360 as embodied by the random emboss pattern of this invention, the film may be taped and the tape may be easily relocated without tearing the film. On the other hand, for a TAV of 100 as possessed by the patented film, the securement of the diaper backsheet to itself is unsatisfactory. Accordingly, from a TAV standpoint, only the film of this invention has relatively equal properties of tape adhesion value on both sides of the film which render it uniquely adaptible for utilization in diaper back operations. In addition, the random emboss film of this invention is the only film that provides a matte finish having substantially equal gloss on both sides in combination with the desirable properties of TAV. For instance, the conventional matte sandblasted film of FIG. 3 has unsatisfactory gloss on 14-22 of the rubber roll side and fairly unsatisfactory gloss on the metal roll side. Gloss is a measure of customer acceptability and soft or cloth-like hand feel. In contrast, the random emboss film of this invention has substantially equal gloss and is very acceptable to the customer. In addition, the film of this invention is very unique in that it has a totally different appearance because of its structure. For instance, the random embossed film of this invention tends to have a soft slight sparkling effect even though it is substantially dull on both sides of the film. It tends to feel softer as well. With reference to the coefficient of friction values (COF), it is to noted that the higher COF values provide a benefit to the use of the random embossed film in packaging operations. For instance, with reference to the 1.5-2 COF value of the random emboss film, as compared to the other values of 1-1.2 of the known films, the COF values for the invention film are considerably higher. This is especially advantageous where a product is to be packaged in the film. For instance, in the course of packaging sanitary napkins having a polyethylene film surface, where such sanitary napkins are placed on a moving film of the type employed in this invention, the sanitary napkin may be placed on the film and held very firmly while it is being conveyed and wrapped in the film. This is an important feature of this invention. Furthermore, the random embossed film has a significantly different COF on both sides namely 0.6-0.8 in contrast to about 1.5-2. Such differences can be very beneficial in packaging applications where one side of the film needs a very high COF and the other side needs a very low COF. In contrast, the films of FIGS. 2 and 3 do not provide such a exceptional difference in COF.

With reference to the above TABLE, therefore, other conventional matte and embossed films do not possess the very unique combinations of TAV, COF or gloss as is achieved in the random embossed film of this invention. There are other unique aspects and differences as well between the random embossed film of this invention and prior films represented by the conventional matte and patented film of FIGS. 2-3. For instance, edge curl is an important consideration and is used to evidence the film web flatness under tension. Under essentially identical conditions, for example, the random embossed pattern of this invention has a very low degree of edge curl, namely, 30-35 degrees as compared to an edge curl propensity of about 45-60 degrees for the patented film above mentioned. This represents approximately 50 to 100 percent improvement in edge curl which enables the random embossed film to be very satisfactorily handled at high speeds on machinery. Such edge curl tests may be simulated by placing a sample of film in a vertical position and uniformly applying stress across its width and determining the extent of the edge curl from 0 to 360 degrees as the edge of the film curls around the end of the sample. Such an improvement in edge curl is a further advantageous feature of the embossed film of this invention.

Other results of this invention are considered to be unpredicted and unobvious in view of the experience of the trade and persons of ordinary skill. For instance, as developed above, it is critically important that the film of this invention be deeply embossed. Thus, for a film thickness of about 0.5 to about 1.5 mils, the overall embossed depth as measured is critically about 0.4 to about 2 mils. This requires some further explanation. Currently the most preferred form of the invention is represented by a sample of low density polyethylene film having a film thickness of about 1-1.2 mils and an overal embossed depth of about 0.8-1.5 mils. Such a film is flat, exhibits essentially no edge curl upon processing, posseses relatively equal TAV on each side, excellent winding and uniform roll characteristics, and is uniquely dull on both sides of the film while having a slight sparkle. It is considered very unexpected that such a film may be so deeply embossed without loss of preferred TAV characteristics. Rather, it has been found that the TAV values on both sides of the film are substantially the same from the standpoint of commercial acceptability. This is indeed surprising. It should be understood that when a thin film on the order of about 0.5 mil is made, that the overall depth of the end product will be closer to about 0.4 and the advantageous results of the invention will be achieved. The overall depth for such a thin film need not be as great obviously as the overall depth of a thicker film in order to provide an advantageous gloss characteristics, for instance. In other words, the gloss and overall embossed depth are not linearly related. Rather gloss is related to film thickness as well. Under these circumstances, for instance, the embossed depth of the film for a preferred film thickness of about 1-1.2 mils is about 0.8-1.5 mils. However, for a film thickness of about 0.5 mils the embossed depth as measured by the TMI Model 549M technique described above would be about 0.4 mil.

During the course of experimentation on the acceptability of the random embossed pattern of this invention and the depth of the emboss, it has been found that even for a 1 mil film that an embossed depth of about 0.3 to about 0.6 is unsatisfactory in that the gloss on one or both sides of the film is unsatisfactory. Furthermore, even at such low embossing depths, tape adhesion values are unsatisfactory or marginly satisfactory on at least one of the sides of the film. Surprisingly and critically, it is when about a 1 mil film is deeply embossed to a level of about 1 mil in embossing depth that the advantages of the invention are best achieved including excellent gloss or cloth-like feel and relatively equal tape adhesion value on both sides of the film.

Having described the above invention in its preferred parameters, various modifications may be made as understood by a person of ordinary skill in this art in view of the specification.

We claim:

1. An embossed thermoplastic film having a random embossed matte pattern which is undetectible to the unaided eye and imparts a visibly dull surface to both sides of the film, said film having a thickness of about 0.5 to about 1.5 mils and an embossed depth of about 0.4 to about 2 mils wherein the random pattern comprises a series of asymmetric raised bosses and asymmetric depressions to provide an overall random network on one side of the film, wherein said random pattern of asymmetric bosses and depressions overlie on the opposite side of said film corresponding asymmetric depressions and asymmetric bosses.

2. The embossed film of claim 1 wherein said thermoplastic is selected from the group consisting of polyethylene, polypropylene, polyester, polystyrene and copolymers thereof.

3. The embossed film of claim 1 having a combination of substantially equal tape adhesion values on both sides of the film and low gloss on both sides of the film especially adapted for diaper applications.

4. The embossed film of claim 3 wherein said film has a thickness of about 1 to about 1.2 mils and an embossed depth of about 0.8 to about 1.5 mils.

5. The embossed film of claim 4 wherein said thermoplastic is a low to medium density polyethylene.

6. The embossed film of claim 1 wherein said bosses and depressions each have an average size ranging from about 3 to about 20 mils in width and length.

7. An embossed thermoplastic polyethylene diaper or pad film for disposable hygenic and surgical fluid barrier applications having a random embossed matte pattern which is undetectible to the unaided eye and imparts a visibly dull surface to both sides of the film, said film having a thickness of about 1 to about 1.2 mils and an embossed depth of about 0.8 to about 1.5 mils wherein the random pattern comprises a series of asymmetric raised bosses and asymmetric depressions to provide an overall random network where the areas of said bosses and depressions are about equal on each side of the film, wherein said random pattern of asymmetric bosses and depressions overlie on the opposite side of said film corresponding asymmetric depressions and asymmetric bosses, wherein said bosses and depressions each have an average size distribution of about 3 to about 20 mils in width and length, said film having a combination of substantially equal tape adhesion values on both sides of the film and low gloss on both sides of the film especially adapted for diaper or pad applications.

* * * * *